United States Patent [19]
Berg et al.

[11] Patent Number: 5,837,008
[45] Date of Patent: Nov. 17, 1998

[54] INTRAVASCULAR STENT AND METHOD

[75] Inventors: Eric P. Berg; Ronald J. Tuch, both of Plymouth; Michael Dror, Edina; Rodney G. Wolff, Minnetonka Beach, all of Minn.

[73] Assignee: Medtronic, Inc., Minneapolis, Minn.

[21] Appl. No.: 429,969

[22] Filed: Apr. 27, 1995

Related U.S. Application Data

[62] Division of Ser. No. 52,878, Apr. 26, 1993, Pat. No. 5,464,650.

[51] Int. Cl.$^6$ ........................................................ A61F 2/06
[52] U.S. Cl. .................................. 623/1; 623/11; 623/12; 606/194; 606/195; 600/36
[58] Field of Search ...................... 600/36; 606/191–200; 623/1, 11–12

[56] References Cited

U.S. PATENT DOCUMENTS

| | | | |
|---|---|---|---|
| 4,292,965 | 10/1981 | Nash et al. | 427/2 |
| 4,529,614 | 7/1985 | Burns | 427/2 |
| 4,532,929 | 8/1985 | Mattel et al. | 427/2 |
| 4,733,665 | 3/1988 | Palmaz . | |
| 4,753,652 | 6/1988 | Langer et al. | 623/1 |
| 4,800,882 | 1/1989 | Gianturco . | |
| 4,886,062 | 12/1989 | Wiktor . | |
| 4,888,009 | 12/1989 | Lederman et al. | 623/2 |
| 4,894,231 | 1/1990 | Moreau et al. | 424/426 |
| 4,955,899 | 9/1990 | Della Corna et al. | 427/2 |
| 5,061,276 | 10/1991 | Tu et al. | 623/1 |
| 5,102,417 | 4/1992 | Palmaz . | |
| 5,176,907 | 1/1993 | Leong | 424/78.08 |
| 5,192,308 | 3/1993 | Ostapchenko | 427/2 |
| 5,221,698 | 6/1993 | Amidon et al. | 427/2 |
| 5,234,456 | 8/1993 | Silvestrini | 606/194 |
| 5,242,391 | 9/1993 | Place et al. | 604/60 |
| 5,290,266 | 3/1994 | Rohling et al. . | |

FOREIGN PATENT DOCUMENTS

| | | |
|---|---|---|
| 9013332 | 11/1990 | WIPO . |
| 9112779 | 6/1991 | WIPO . |
| 9116102 | 10/1991 | WIPO . |
| 9117789 | 11/1991 | WIPO . |
| 9118940 | 12/1991 | WIPO . |
| 9215286 | 9/1992 | WIPO . |
| 9306792 | 4/1993 | WIPO . |

OTHER PUBLICATIONS

*Seeding of Intravascular Stents with Genetically Engineered Endothelial Cells,* by Dicket et al., in Circulations, vol. 80, No. 5, Nov. 1989.

*Restenosis and the Proportinal Neointimal Response to Coronary Artery Injury: Results in a Porcine Model,* by Schwartz et al., in JACC, vol. 19, No. 2, Feb. 1992, pp. 267–274.

*Restenosis After Balloon Angioplasty,* by Schwartz, et al., in Circulation, vol. 82, No. 6, Dec. 1990.

*Primary Examiner*—Mickey Yu
*Assistant Examiner*—Francis K. Cuddihy
*Attorney, Agent, or Firm*—Daniel W. Latham; Harold R. Patton

[57] ABSTRACT

A method for making an intravascular stent by applying to the body of a stent a solution which includes a solvent, a polymer dissolved in the solvent and a therapeutic substance dispersed in the solvent and then evaporating the solvent. The inclusion of a polymer in intimate contact with a drug on the stent allows the drug to be retained on the stent during expansion of the stent and also controls the administration of drug following implantation. The adhesion of the coating and the rate at which the drug is delivered can be controlled by the selection of an appropriate bioabsorbable or biostable polymer and the ratio of drug to polymer in the solution. By this method, drugs such as dexamethasone can be applied to a stent, retained on a stent during expansion of the stent and elute at a controlled rate.

36 Claims, 3 Drawing Sheets

INTRAVASCULAR STENT AND METHOD

This application is a Divisional of U.S. application Ser. No. 08/052,878, filed Apr. 26, 1993, now U.S. Pat. No. 5,464,650.

BACKGROUND OF THE INVENTION

This invention relates to intravascular stents for treatment of injuries to blood vessels and particularly to stents having a framework onto which a therapeutic substance or drug is applied.

Although angioplasty procedures have increased greatly in popularity for treatment of occluded arteries, the problem of restenosis following the angioplasty treatment remains a significant problem. Restenosis is the closure of a peripheral or coronary artery following trauma to the artery caused by efforts to open an occluded portion of the artery by angioplasty, such as, for example, by balloon dilation, atherectomy or laser ablation treatment of the artery. For these angioplasty procedures, restenosis occurs at a rate of about 30–60% depending upon the vessel location, lesion length and a number of other variables.

One aspect of restenosis may be simply mechanical; e.g. caused by the elastic rebound of the arterial wall and/or by dissections in the vessel wall caused by the angioplasty procedure. These mechanical problems have been successfully addressed by the use of stents to tack-up dissections and prevent elastic rebound of the vessel, thereby reducing the level of restenosis for many patients. The stent is typically inserted by catheter into a vascular lumen and expanded into contact with the diseased portion of the arterial wall, thereby providing internal support for the lumen. Examples of stents which have been successfully applied over a PTCA balloon and radially expanded at the same time as the balloon expansion of an affected artery include the stents disclosed in U.S. Pat. No. 4,733,665 issued to Palmaz, U.S. Pat. No. 4,800,882 issued to Gianturco and U.S. Pat. No. 4,886,062 issued to Wiktor which are incorporated herein by reference in their entirety.

Another aspect of restenosis is believed to be a natural healing reaction to the injury of the arterial wall that is caused by angioplasty procedures. The final result of the complex steps of the healing process is intimal hyperplasia, the migration and proliferation of medial smooth muscle cells, until the artery is again occluded.

To address both aspects of the restenosis problem, it has been proposed to provide stents which are seeded with endothelial cells (Dichek, D. A. et al Seeding of Intravascular Stents With Genetically Engineered Endothelial Cells; Circulation 1989; 80: 1347–1353). In that experiment, sheep endothelial cells that had undergone retrovirus-mediated gene transfer for either bacterial beta-galactosidase or human tissue-type plasminogen activator were seeded onto stainless steel stents and grown until the stents were covered. The cells were therefore able to be delivered to the vascular wall where they could provide therapeutic proteins. Other methods of providing therapeutic substances to the vascular wall include simple heparin-coated metallic stents, whereby a heparin coating is ionically or covalently bonded to the stent. Still other methods of providing therapeutic substances to the vascular wall by means of stents have also been proposed such as in U.S. Pat. No. 5,102,417 issued to Palmaz or in international patent application WO 91/12779 "Intraluminal Drug Eluting Prosthesis" and international patent application WO 90/13332 "Stent With Sustained Drug Delivery". In those applications, it is suggested that antiplatelet agents, anticoagulant agents, antimicrobial agents, antimetabolic agents and other drugs could be supplied in stents to reduce the incidence of restenosis.

Metal stents such as those disclosed in U.S. Pat. No. 4,733,665 issued to Palmaz, U.S. Pat. No. 4,800,882 issued to Gianturco or U.S. Pat. No. 4,886,062 issued to Wiktor could be suitable for drug delivery in that they are capable of maintaining intimate contact between a substance applied to the outer surface of the stent and the tissues of the vessel to be treated. However, there are significant problems to be overcome in order to secure a therapeutically significant amount of a substance onto the metal of the stent; to keep it on the stent during expansion of the stent into contact with the blood vessel wall; and also controlling the rate of drug delivery from the drug on the stent to the vessel wall.

It is therefore an object of the present invention to provide a stent having a therapeutically significant amount of a drug applied thereto.

It is also an object of the present invention to provide a stent which may be delivered and expanded in a selected blood vessel without losing a therapeutically significant amount of a drug applied thereto.

It is also an object of the present invention to provide a drug-containing stent which allows for a sustained release of the drug to vascular tissue.

It is also an object of the present invention to provide a simple method for applying to a stent a coating of a therapeutic substance.

SUMMARY OF THE INVENTION

These and other objects are accomplished by the present invention. We have discovered a method for making an intravascular stent by applying to the body of a stent, and in particular to its tissue-contacting surface, a solution which includes a solvent, a polymer dissolved in the solvent and a therapeutic substance dispersed in the solvent and then evaporating the solvent. The inclusion of a polymer in intimate contact with a drug on the stent allows the drug to be retained on the stent in a resilient matrix during expansion of the stent and also slows the administration of drug following implantation. The method can be applied whether the stent has a metallic or polymeric surface. The method is also an extremely simple method since it can be applied by simply immersing the stent into the solution or by spraying the solution onto the stent. The amount of drug to be included on the stent can be readily controlled by applying multiple thin coats of the solution while allowing it to dry between coats. The overall coating should be thin enough so that it will not significantly increase the profile of the stent for intravascular delivery by catheter. It is therefore preferably less than about 0.002 inch thick and most preferably less than 0.001 inch thick. The adhesion of the coating and the rate at which the drug is delivered can be controlled by the selection of an appropriate bioabsorbable or biostable polymer and by the ratio of drug to polymer in the solution. By this method, drugs such as glucocorticoids (e.g. dexamethasone, betamethasone), heparin, hirudin, tocopherol, angiopeptin, aspirin, ACE inhibitors, growth factors, oligonucleotides, and, more generally, antiplatelet agents, anticoagulant agents, antimitotic agents, antioxidants, antimetabolite agents, and anti-inflammatory agents can be applied to a stent, retained on a stent during expansion of the stent and elute the drug at a controlled rate. The release rate can be further controlled by varying the ratio of drug to polymer in the multiple layers. For example, a higher drug-to-polymer ratio in the outer layers than in the inner layers would result in a higher early dose which would decrease over time.

In operation, the stent made according to the present invention can deliver drugs to a body lumen by introducing the stent transluminally into a selected portion of the body lumen and radially expanding the stent into contact with the body lumen. The transluminal delivery can be accomplished by a catheter designed for the delivery of stents and the radial expansion can be accomplished by balloon expansion of the stent, by self-expansion of the stent, or a combination of self-expansion and balloon expansion.

DETAILED DESCRIPTION OF THE INVENTION

Figure 3:
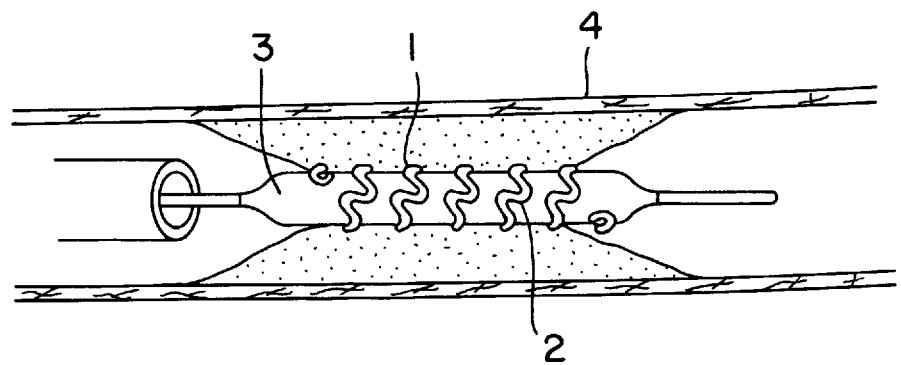
FIG. 3 shows a balloon and stent assembly according to U.S. Pat. No. 4,886,062 inside a partially occluded vessel.

The present invention relates to a method for making an intravascular stent. The underlying structure of the stent can be virtually any stent design, whether of the self-expanding type or of the balloon-expandable type and whether metal or polymeric. Thus metal stent designs such as those disclosed in U.S. Pat. No. 4,733,665 issued to Palmaz, U.S. Pat. No. 4,800,882 issued to Gianturco or U.S. Pat. No. 4,886,062 issued to Wiktor could be used in the present invention. For example, the configuration of the stent 1 shown in FIG. 3 is such, that a wire has a reversing bend pattern 2 so that controlled radial expansion of the stent 1 is accomplished by the force generated by an inflating balloon 3. When acted upon by the inflating balloon 3, the stent 1 expands radially by controlled deformation and tension applied to the pattern 2 of the wire. The expanded larger diameter will conform to the inside of the vessel 4 and maintain intimate contact with the inside wall due to the low memory level of the deformable metal used for the wire. The stent could be made of virtually any bio-compatible material having physical properties suitable for the design. For example, tantalum and stainless steel have been proven suitable for many such designs and could be used in the present invention. Also, stents made with biostable or bioabsorbable polymers such as poly(ethylene terephthalate), polyacetal, poly(lactic acid), poly(ethylene oxide)/poly(butylene terephthalate) copolymer could be used in the present invention. Although the stent surface should be clean and free from contaminants that may be introduced during manufacturing, the stent surface requires no particular surface treatment in order to retain the coating applied in the present invention. Both the inner and outer surfaces of the stent may be provided with the coating according to the present invention.

In order to provide the coated stent according to the present invention, a solution which includes a solvent, a polymer dissolved in the solvent and a therapeutic substance dispersed in the solvent is first prepared. It is important to choose a solvent, a polymer and a therapeutic substance that are mutually compatible. It is essential that the solvent is capable of placing the polymer into solution at the concentration desired in the solution. It is also essential that the solvent and polymer chosen do not chemically alter the therapeutic character of the therapeutic substance. However, the therapeutic substance only needs to be dispersed throughout the solvent so that it may be either in a true solution with the solvent or dispersed in fine particles in the solvent. Examples of some suitable combinations of polymer, solvent and therapeutic substance are set forth in Table 1 below.

TABLE 1

| POLYMER | SOLVENT | THERAPEUTIC SUBSTANCE |
| --- | --- | --- |
| poly(L-lactic acid) | chloroform | dexamethasone |
| poly(lactic acid-co-glycolic acid) | acetone | dexamethasone |
| polyether urethane | N-methyl pyrrolidone | tocopherol (vitamin E) |
| silicone adhesive | xylene | dexamethasone phosphate |
| poly(hydroxy--butyrate-co--hydroxyvalerate) | dichloro--methane | aspirin |
| fibrin | water (buffered saline) | heparin |

The solution is applied to the stent and the solvent is allowed to evaporate, thereby leaving on the stent surface a coating of the polymer and the therapeutic substance. Typically, the solution can be applied to the stent by either spraying the solution onto the stent or immersing the stent in the solution. Whether one chooses application by immersion or application by spraying depends principally on the viscosity and surface tension of the solution, however, it has been found that spraying in a fine spray such as that available from an airbrush will provide a coating with the greatest uniformity and will provide the greatest control over the amount of coating material to be applied to the stent. In either a coating applied by spraying or by immersion, multiple application steps are generally desirable to provide improved coating uniformity and improved control over the amount of therapeutic substance to be applied to the stent.

The polymer chosen must be a polymer that is biocompatible and minimizes irritation to the vessel wall when the stent is implanted. The polymer may be either a biostable or a bioabsorbable polymer depending on the desired rate of release or the desired degree of polymer stability, but a bioabsorbable polymer is probably more desirable since, unlike a biostable polymer, it will not be present long after implantation to cause any adverse, chronic local response. Bioabsorbable polymers that could be used include poly(L-lactic acid), polycaprolactone, poly(lactide-co-glycolide), poly(hydroxybutyrate), poly(hydroxybutyrate-co-valerate), polydioxanone, polyorthoester, polyanhydride, poly (glycolic acid), poly(D,L-lactic acid), poly(glycolic acid-co-trimethylene carbonate), polyphosphoester, polyphosphoester urethane, poly(amino acids), cyanoacrylates, poly (trimethylene carbonate), poly(iminocarbonate), copoly (ether-esters) (e.g. PEO/PLA), polyalkylene oxalates, polyphosphazenes and biomolecules such as fibrin, fibrinogen, cellulose, starch, collagen and hyaluronic acid. Also, biostable polymers with a relatively low chronic tissue response such as polyurethanes, silicones, and polyesters could be used and other polymers could also be used if they can be dissolved and cured or polymerized on the stent such as polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

The ratio of therapeutic substance to polymer in the solution will depend on the efficacy of the polymer in securing the therapeutic substance onto the stent and the rate at which the coating is to release the therapeutic substance to the tissue of the blood vessel. More polymer may be needed if it has relatively poor efficacy in retaining the therapeutic substance on the stent and more polymer may be needed in order to provide an elution matrix that limits the elution of a very soluble therapeutic substance. A wide ratio of therapeutic substance to polymer could therefore be appropriate and could range from about 10:1 to about 1:100.

The therapeutic substance used in the present invention could be virtually any therapeutic substance which possesses desirable therapeutic characteristics for application to a blood vessel. This can include both solid substances and liquid substances. For example, glucocorticoids (e.g. dexamethasone, betamethasone), heparin, hirudin, tocopherol, angiopeptin, aspirin, ACE inhibitors, growth factors, oligonucleotides, and, more generally, antiplatelet agents, anticoagulant agents, antimitotic agents, antioxidants, antimetabolite agents, and anti-inflammatory agents could be used. Antiplatelet agents can include drugs such as aspirin and dipyridamole. Aspirin is classified as an analgesic, antipyretic, anti-inflammatory and antiplatelet drug. Dypridimole is a drug similar to aspirin in that it has anti-platelet characteristics. Dypridimole is also classified as a coronary vasodilator. Anticoagulant agents can include drugs such as heparin, coumadin, protamine, hirudin and tick anticoagulant protein. Antimitotic agents and antimetabolite agents can include drugs such as methotrexate, azathioprine, vincristine, vinblastine, fluorouracil, adriamycin and mutamycin.

The following examples are exemplary of various aspects of the invention.

EXAMPLE 1

A 1% solution of dexamethasone in acetone was made, forming a clear solution. The solution was placed in an airbrush reservoir (Badger #200). Wiktor type tantalum wire stents were sprayed with the solution in short bursts while rotating the stents. The acetone quickly evaporated from the stents, leaving a white residue on the stent wire. The process was continued until all of the stent wires were coated. The drug elution rate for the stent was determined by immersing the stent in phosphate buffered saline solution (pH=7.4). Traces of dexamethasone were observed to remain on the immersed stents for less than 31 hours.

EXAMPLE 2

A 2% solution of dexamethasone in acetone was made, forming a solution with suspended particles of dexamethasone. The solution was placed into a tube. Wiktor type tantalum wire stents were dipped rapidly and were allowed to dry. Each stent was dipped into the solution 12–15 times to provide a white surface coating. Two stents were placed on an angioplasty balloon and were inflated on the balloon. Approximately 80% of the dexamethasone coating flaked off of the stents.

EXAMPLE 3

A solution of 1% dexamethasone and 0.5% poly (caprolactone) (Aldrich 18,160-9) in acetone was made. The solution was placed into a tube. Wiktor type tantalum wire stents were dipped rapidly and were allowed to dry. Each stent was dipped into the solution 12–15 times to provide a white surface coating. A stent so coated was expanded on a 3.5 mm angioplasty balloon causing a significant amount of the coating to become detached.

EXAMPLE 4

A solution of 1% dexamethasone and 0.5% poly(L-lactic acid) (Medisorb) in acetone was made. The solution was placed into a tube. Wiktor type tantalum wire stents were dipped rapidly and were allowed to dry. Each stent was dipped into the solution 12–15 times to provide a white surface coating. A stent so coated was expanded on a 3.5 mm angioplasty balloon causing only a small portion of the coating (less than 25%) to become detached)

EXAMPLE 5

A solution including a 2% dispersion of dexamethasone and a 1% solution of poly(L-lactic acid) (CCA Biochem MW=550,000) in chloroform was made. The solution was placed into an airbrush (Badger). Wiktor type tantalum wire stents were sprayed in short bursts and were allowed to dry. Each stent was sprayed with the solution about 20 times to provide a white surface coating. A stent so coated was expanded on a 3.5 mm angioplasty balloon. The coating remained attached to the stent throughout the procedure.

EXAMPLE 6

Figure 1:
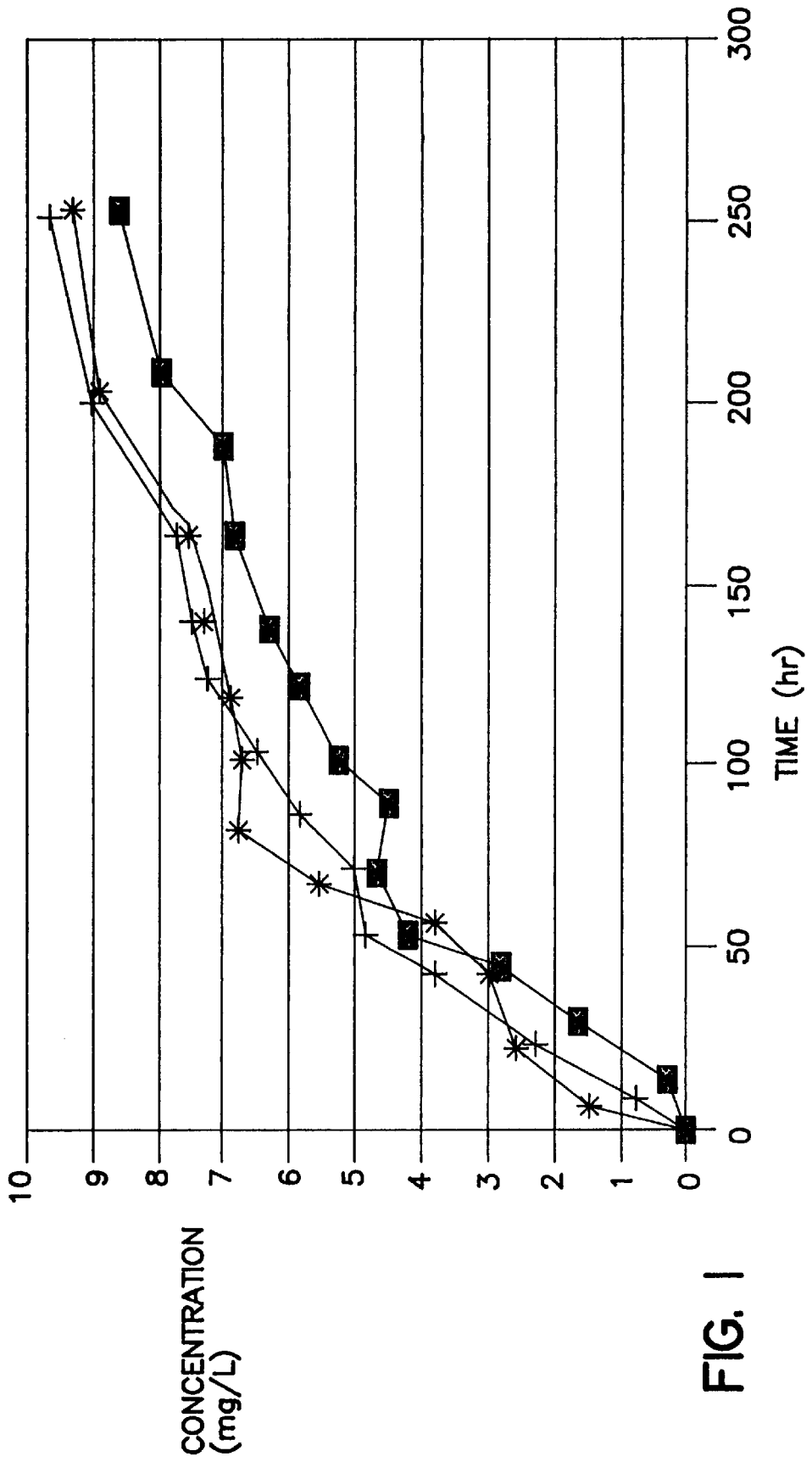
FIG. 1 is a plot showing elution profiles for stents according to the present invention with a coating of dexamethasone and poly(L-lactic acid) made according to Example 6.

A solution including a 2% dispersion of dexamethasone and a 1% solution of poly(L-lactic acid) (CCA Biochem MW=550,000) in chloroform was made. The solution was placed into an airbrush (Badger #250-2). Wiktor type tantalum wire stents were suspended from a fixture and sprayed in 24 short bursts (6 bursts from each of the four directions perpendicular to the stent axis) and were allowed to dry. The resulting stents had a coating weight of about 0.0006–0.0015 grams. Three of the stents were tested for long term elution by placing one stent in 3.0 ml of phosphate buffered saline solution (pH=7.4) at room temperature without stirring. The amount of dexamethasone eluted was evaluated by measuring absorbance at 244 nm in a UV-VIS spectrophotometer. The results of this test are given in FIG. 1.

EXAMPLE 7

Figure 2:
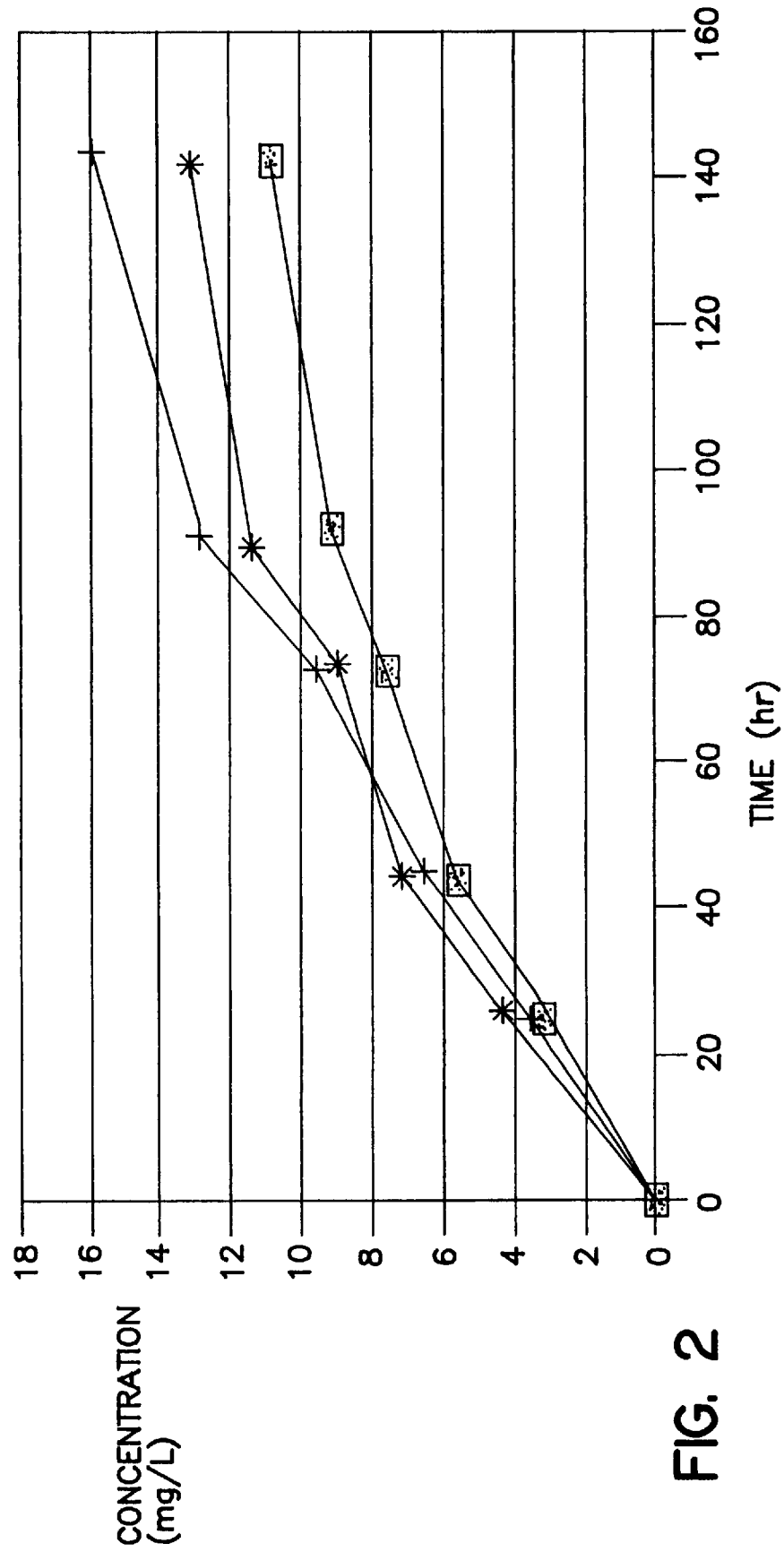
FIG. 2 is a plot showing elution profiles for sterilized stents according to the present invention with a coating of dexamethasone and poly(L-lactic acid) made according to Example 7.

A solution including a 2% dispersion of dexamethasone and a 1% solution of poly(L-lactic acid) (Medisorb 100-L) in chloroform was made along with a control solution of 1% of poly(L-lactic acid) (Medisorb 100-L) in chloroform. The solutions was placed into an airbrush (Badger #250-2). Wiktor type tantalum wire stents were expanded on a 3.0 mm balloon, suspended from a fixture and sprayed in 16 short bursts (2–3 bursts of about 1 second followed by several minutes drying time between applications). The resulting dexamethasone-coated stents had an average coating weight of about 0.0012 grams while the polymer-coated stents had an average polymer weight of about 0.0004 grams. The stents were sterilized in ethylene oxide. Three of the sterilized dexamethasone-coated stents were tested for long term elution by placing one stent in 3.0 ml of phosphate buffered saline solution (pH=7.4 ) at room temperature without stirring. The amount of dexamethasone eluted was evaluated by measuring absorbance at 244 nm in a UV-VIS spectrophotometer. The results of this test are given in FIG. 2. Dexamethasone-coated stents and polymer-coated control stents were implanted in the coronary arteries of 8 pigs (N=12 for each type) according to the method set forth in "Restenosis After Balloon Angioplasty—A Practical Proliferative Model in Porcine Coronary Arteries," by Robert S. Schwartz, et al, *Circulation* 82(6):2190–2200, December 1990, and "Restenosis and the Proportional Neointimal Response to Coronary Artery Injury: Results in a Porcine Model" by Robert S. Schwartz et al, *J Am Coll Cardiol;* 19;267–74 February 1992 with the result that when compared with the controls, the dexamethasone-coated stents reduced the amount of proliferation associated with the arterial injury.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive concepts.

We claim:

1. A method for delivery of a therapeutic substance to the interior of a body lumen comprising the steps of:
    (a) providing a generally cylindrical, radially expandable stent body having a surface;
    (b) applying to the surface a solution which includes a solvent, a polymer dissolved in the solvent and a therapeutic substance dispersed in the solvent;
    (c) evaporating the solvent to provide a coat of therapeutic substance and polymer on the surface;
    (d) repeating steps (b) and (c) until a plurality of coats of therapeutic substance and polymer are on the surface;
    (e) introducing the stent body and the plurality of coats of therapeutic substance and polymer transluminally into a selected portion of the body lumen; and
    (f) radially expanding the stent body and the plurality of coats of therapeutic substance and polymer into contact with the body lumen such that the plurality of coats of therapeutic substance and polymer are retained on the surface.

2. A method according to claim 1 wherein the surface is a polymeric surface.

3. A method according to claim 1 wherein the solution is applied by spraying.

4. A method according to claim 1 wherein the solution is applied by immersion.

5. A method according to claim 1 wherein the polymer is a bioabsorbable polymer.

6. A method according to claim 5 wherein the polymer is selected from the group consisting of poly(L-lactic acid), poly(lactide-co-glycolide) and poly(hydroxybutyrate-co-valerate).

7. A method according to claim 1 wherein the polymer is a biostable polymer.

8. A method according to claim 7 wherein the polymer is selected from the group consisting of silicones, polyurethanes, polyesters, vinyl homopolymers and copolymers, acrylate homopolymers and copolymers, polyethers and cellulosics.

9. A method according to claim 1 wherein the ratio of therapeutic substance to dissolved polymer in the solution is in the range of about 10:1 to 1:100.

10. A method according to claim 1 wherein the therapeutic substance is selected from the group consisting of glucocorticoids, dexamethasone, dexamethasone sodium phosphate, anticoagulants, heparin, hirudin, tick anticoagulant peptide, angiopeptin, antimitotic agents, and oligonucleotides.

11. A method for delivery of a therapeutic substance to the interior of a body lumen comprising the steps of:
    (a) providing a generally cylindrical, radially expandable stent body having a metal surface;
    (b) applying to the metal surface a solution which includes a solvent, a polymer dissolved in the solvent and a therapeutic substance dispersed in the solvent;
    (c) evaporating the solvent to provide a coat of therapeutic substance and polymer on the metal surface;
    (d) repeating steps (b) and (c) until a plurality of coats of therapeutic substance and polymer are on the metal surface;
    (e) introducing the stent body and the plurality of coats of therapeutic substance and polymer transluminally into a selected portion of the body lumen; and
    (f) radially expanding the stent body and the plurality of coats of therapeutic substance and polymer into contact with the body lumen such that the plurality of coats of therapeutic substance and polymer are retained on the metal surface.

12. A method according to claim 11 wherein the metal surface is a low memory metal surface.

13. A method according to claim 11 wherein the metal surface is a stainless steel surface.

14. A method according to claim 11 wherein the metal surface is a tantalum surface.

15. A method according to claim 11 wherein the metal surface is a metal wire surface.

16. A method according to claim 11 wherein the metal surface comprises a plurality of reversing bends which permits the stent body to be expanded from a first diameter to a second, expanded diameter.

17. A method according to claim 11 wherein the metal surface is on an interior portion of the stent body.

18. A method according to claim 11 wherein the metal surface is on an exterior portion of the stent body.

19. A method according to claim 11 wherein the solution is applied by spraying.

20. A method according to claim 11 wherein the solution is applied by immersion.

21. A method according to claim 11 wherein the polymer is a bioabsorbable polymer.

22. A method according to claim 21 wherein the polymer is selected from the group consisting of poly(L-lactic acid), poly(lactide-co-glycolide) and poly(hydroxybutyrate-co-valerate).

23. A method according to claim 11 wherein the polymer is a biostable polymer.

24. A method according to claim 23 wherein the polymer is selected from the group consisting of silicones, polyurethanes, polyesters, vinyl homopolymers and copolymers, acrylate homopolymers and copolymers, polyethers and cellulosics.

25. A method according to claim 11 wherein the ratio of therapeutic substance to dissolved polymer in the solution is in the range of about 10:1 to 1:100.

26. A method according to claim 11 wherein the therapeutic substance is selected from the group consisting of glucocorticoids, dexamethasone, dexamethasone sodium phosphate, anticoagulants, heparin, hirudin, tick anticoagulant peptide, angiopeptin, antimitotic agents, and oligonucleotides.

27. A method for delivery of a therapeutic substance to the interior of a body lumen comprising the steps of:
   (a) providing a generally cylindrical, radially expandable stent body having a surface;
   (b) applying to the surface a solution which includes a solvent, a polymer dissolved in the solvent and a therapeutic substance dispersed in the solvent;
   (c) evaporating the solvent to provide a coat of therapeutic substance and polymer on the surface;
   (d) repeating steps (b) and (c) until a plurality of coats of therapeutic substance and polymer are on the surface such that the ratio of therapeutic substance to dissolved polymer is varied in the plurality of coats;
   (e) introducing the stent body and the plurality of coats of therapeutic substance and polymer transluminally into a selected portion of the body lumen; and
   (f) radially expanding the stent body and the plurality of coats of therapeutic substance and polymer into contact with the body lumen such that the plurality of coats of therapeutic substance and polymer are retained on the metal surface.

28. A method according to claim 27 wherein the ratio of therapeutic substance to dissolved polymer is higher in an outer coat than in an inner coat.

29. A method according to claim 27 wherein the solution is applied by spraying.

30. A method according to claim 27 wherein the solution is applied by immersion.

31. A method according to claim 27 wherein the polymer is a bioabsorbable polymer.

32. A method according to claim 31 wherein the polymer is selected from the group consisting of poly(L-lactic acid), poly(lactide-co-glycolide) and poly(hydroxybutyrate-co-valerate).

33. A method according to claim 27 wherein the polymer is a biostable polymer.

34. A method according to claim 33 wherein the polymer is selected from the group consisting of silicones, polyurethanes, polyesters, vinyl homopolymers and copolymers, acrylate homopolymers and copolymers polyethers and cellulosics.

35. A method according to claim 27 wherein the ratio of therapeutic substance to dissolved polymer in the solution is in the range of about 10:1 to 1:100.

36. A method according to claim 27 wherein the therapeutic substance is selected from the group consisting of glucocorticoids, dexamethasone, dexamethasone sodium phosphate, anticoagulants, heparin, hirudin, tick anticoagulant peptide, angiopeptin, antimitotic agents, and oligonucleotides.

* * * * *